United States Patent [19]

Colle et al.

[11] Patent Number: 5,036,094
[45] Date of Patent: Jul. 30, 1991

[54] AZOLYL-DERIVATIVES ENDOWED WITH ANTIFUNGAL ACTIVITY

[75] Inventors: Roberto Colle; Giovanni Camaggi; Franco Gozzo; Giuseppina Ratti; Luigi Mirenna; Carlo Garavaglia, all of Milan, Italy

[73] Assignee: Montedison S.p.A., Milan, Italy

[21] Appl. No.: 408,945

[22] Filed: Sep. 18, 1989

Related U.S. Application Data

[63] Continuation of Ser. No. 911,217, Sep. 24, 1986, abandoned.

[30] Foreign Application Priority Data

Nov. 4, 1985 [IT] Italy ............... 22705 A/85

[51] Int. Cl.$^5$ ............... A01N 43/653; C07D 405/06; C07D 249/08
[52] U.S. Cl. ............... 514/383; 548/267.8; 548/268.6; 548/268.8
[58] Field of Search ............ 514/383; 548/262, 267.8, 548/268.6, 268.8

[56] References Cited

U.S. PATENT DOCUMENTS

| | | | |
|---|---|---|---|
| 4,388,327 | 7/1982 | Heeres et al. | 548/262 |
| 4,559,355 | 12/1985 | Kraatz et al. | 548/262 |
| 4,616,027 | 10/1986 | Richardson et al. | 548/262 |
| 4,715,887 | 12/1987 | Kramer et al. | 548/262 |
| 4,810,718 | 3/1989 | Colle et al. | 514/383 |

FOREIGN PATENT DOCUMENTS 2098607  11/1982  United Kingdom ............... 548/262

*Primary Examiner*—Mary C. Lee
*Assistant Examiner*—Patricia L. Morris
*Attorney, Agent, or Firm*—Morgan & Finnegan

[57] ABSTRACT

Disclosed are compounds, having the general formula:

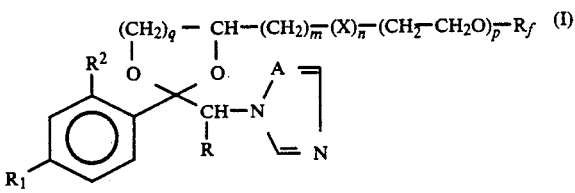

wherein:
m=0, 1, 2; n=0, 1 with the condition that when m=0, also n=0;
p=0, 1; q=1, 2;
X is either oxygen or sulphur;
A=N, CH;
R is H, $CH_3$, F;
$R_1$ is selected from chlorine, bromine, fluorine, $CF_3$, phe=nyl, $C_1$-$C_2$-alkoxy, $C_1$-$C_2$-haloalkoxy, alkylthio, haloalkyl=thio, wherein the halogen is Cl, Br, F;
$R_2$ is selected from H, chlorine, bromine, fluorine;
$R_f$ is selected from the group formed by alkyls containing from 2 to 4 carbon atoms, and containing at least 4 atoms of halogen selected from F, Cl and Br, of which at least 3 are F atoms; alkenyls and alkynyls containing up to 4 carbon atoms, containing at least 2 F atoms and, optionally, other halogens selected between Cl and Br.

The present invention relates to azolyl-derivatives, more particularly to substituted azolyldioxanes and azolyldioxolanes, endowed with high fungicidal activity, to the process for their preparation, and to their related use in the agrarian field.

6 Claims, No Drawings

AZOLYL-DERIVATIVES ENDOWED WITH ANTIFUNGAL ACTIVITY

This application is a continuation of Ser. No. 911,217, filed Sept. 24, 1986, now abandoned.

BACKGROUND OF THE INVENTION

From U.S. Pat. No. 4,338,327 triazolyldioxolanes are known, having the general formula:

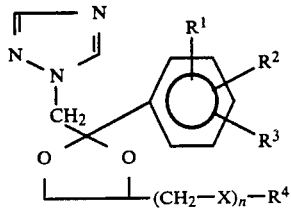

wherein:

$R^1$, $R^2$, $R^3$ are, independently, H, alkyl, alkoxy, halogen, $NO_2$, CN, $CF_3$;

n = 0, 1;

X = O, S;

$R^4$ is alkyl, mono-, di- and tri-haloalkyl, alkyloxyalkyl, mono-, di- and tri-haloalkyloxyalkyl, lower alkenyl, 2-propynyl, 3-halo-2-propynyl, cycloalkyl, aryl, arylalkyl, or arylalkenyl.

In the patent, however, no examples are reported wherein $R^4$ is either a di- or a tri-haloalkyl, or a di- or a tri-halo-alkyloxyalkyl. Furthermore, no such indications are reported on the trend of the fungicidal activity, as to demonstrate a superiority of the compounds wherein $R^4$ contains a halogen atom, relative to the other compounds wherein $R^4$ is not halogenated.

DESCRIPTION OF THE INVENTION

We have found now a class of azolyl-dioxanes and olyl-dioxolanes substituted with alkyl, alkenyl, alkyloxyalkyl and alkyloxyalkenyl groups, all of them being polyfluorinated, endowed with higher fungicidal activity.

An object of the present invention are therefore the compounds, having the general formula:

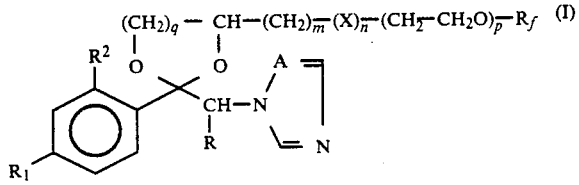

wherein:

m = 0, 1, 2; n = 0, 1 with the condition that when m = 0, also n = 0;

p = 0, 1; q = 1, 2;

X is either oxygen or sulphur;

A = N, CH;

R is H, $CH_3$, F;

$R_1$ is selected from chlorine, bromine, fluorine, $CF_3$, phenyl, $C_1$-$C_2$-alkoxy, $C_1$-$C_2$-haloalkoxy, alkylthio, haloalkylthio, wherein the halogen is Cl, Br, F;

$R_2$ is selected from H, chlorine, bromine, fluorine;

$R_f$ is selected from the group formed by alkyls containing from 2 to 4 carbon atoms, and containing at least 4 atoms of halogen selected from F, Cl and Br, of which at least 3 are F atoms; alkenyls and alkynyls containing up to 4 carbon atoms, containing at least 2 F atoms and, optionally, other halogens selected between Cl and Br.

Examples of $R_f$ groups which can be introduced, according to the present invention, and which are indicated to non-limitative purposes are:

alkyls: —$CF_2$—$CF_3$, —$CF_2$—$CF_2H$, —CFH—$CF_3$, —$CCl_2$—$CF_3$, —$CF_2$—CFHCl, —$CF_2$—$CF_2$—$CF_3$, —$CF_2$—$CF_2$—$CF_2$—$CF_3$, —$CF_2$—CFH—$CF_3$, $CF_2$—$C(CF_3)_2$;

alkenyls: —CF=$CF_2$, —CF=CF—$CF_3$. —CH=CF—$CF_3$, —CH=CCl—$CF_3$, —CH=CBr—$CF_3$, —CH=$C(CF_3)_2$;

alkynyls —C≡C—$CF_3$.

The compounds according to the present invention contain at least 2 chiral centers.

These compounds are generally obtained as mixtures of diastereoisomers. These mixtures can be separated into the individual diastereoisomers by such physical methods as, e.g., column-chromatographies. Inside each pair of diastereoisomers, the individual enantiomers can be separated by methods known from technical literature.

Both the diastereoisomers obtained by chromatographic separation, and the individual enantiomers are an object of the present invention.

An object of the present invention are also:
the salts of the compounds having general formula (I) derived from an inorganic acid, such as a hydrogen e.g., hydriodic, hydrobromic, hydrochloric acid; sulphuric, nitric, thiocyanic and phosphoric acid; or from an organic acid, such as acetic, propanoic, hydroxyacetic, 2-hydroxypropanoic, 2-oxopropanoic, ethanedioic, propanedioic, butanedioic, benzoic, methanesulphonic, 4-methylbenzenesulphonic acid, etc.;
the metal complexes obtained by the reaction of complexation between the derivatives of type (I) with an organic or inorganic salt of a metal, such as halide, nitrate, sulphate, phosphate of, e.g., copper, manganese, zinc or iron.

Examples of compounds of general formula (I) according to the present invention are reported in Table 1.

The compounds reported in Table 1, unless otherwise indicated, should be intended as being mixtures of diastereoisomers.

TABLE 1

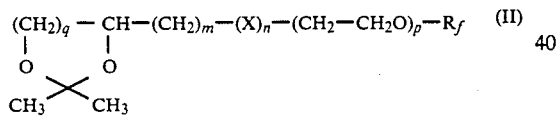

| Compound No. | | R | R₁ | R₂ | m | n | p | q | X | A | $R_f$ |
|---|---|---|---|---|---|---|---|---|---|---|---|
| 1 | (Diastereoisomer A) | H | Cl | Cl | 1 | 1 | zero | 1 | O | N | $-CF_2-CF_2H$ |
| 2 | (Diastereoisomer B) | H | Cl | Cl | 1 | 1 | zero | 1 | O | N | $-CF_2-CF_2H$ |
| 3 | (Mixture of diastereoisomers A + B) | H | Cl | Cl | 1 | 1 | zero | 1 | O | N | $-CF_2-CF_2H$ |
| 4 | | H | Cl | H | 1 | 1 | zero | 1 | O | N | $-CF_2-CF_2H$ |
| 5 | | H | Cl | H | 1 | 1 | zero | 1 | O | N | $-CF=CF-CF_3$ |
| 6 | | H | Cl | H | 1 | 1 | zero | 1 | O | N | $-CF_2-CFH-CF_3$ |
| 7 | | H | Cl | Cl | 1 | 1 | zero | 1 | O | N | $-CF=CF-CF_3$ |
| 8 | | H | Cl | Cl | 1 | 1 | zero | 1 | O | N | $-CF_2-CFH-CF_3$ |
| 9 | | H | Cl | H | 2 | 1 | zero | 1 | O | N | $-CF_2-CF_2H$ |
| 10 | | H | Cl | Cl | 2 | 1 | zero | 1 | O | N | $-CF_2-CF_2H$ |
| 11 | | H | F | F | 1 | 1 | zero | 1 | O | N | $-CF_2-CF_2H$ |
| 12 | (Diastereoisomer A) | H | Cl | Cl | 1 | 1 | zero | 1 | O | CH | $-CF_2-CF_2H$ |
| 13 | (Diastereoisomer B) | H | Cl | Cl | 1 | 1 | zero | 1 | O | CH | $-CF_2-CF_2H$ |
| 14 | (Mixture of diastereoisomers A + B) | H | Cl | Cl | 1 | 1 | zero | 1 | O | CH | $-CF_2-CF_2H$ |
| 15 | | H | Cl | H | 2 | 1 | zero | 1 | O | N | $-CF_2-CFH-CF_3$ |
| 16 | | H | Cl | Cl | 2 | 1 | zero | 1 | O | N | $-CF_2-CFH-CF_3$ |
| 17 | | H | Cl | Cl | 1 | 1 | zero | 1 | O | N | $-CF_2-CFH-Cl$ |
| 18 | | H | Cl | Cl | 1 | 1 | zero | 1 | O | N | $-CF=CFCl$ |
| 19 | (Diastereoisomer A) | H | Cl | Cl | 1 | 1 | 1 | 1 | O | N | $-CF_2-CF_2H$ |
| 20 | (Mixture of diastereoisomer A + B) | H | Cl | Cl | 1 | 1 | 1 | 1 | O | N | $-CF_2-CF_2H$ |
| 21 | | H | Cl | Cl | 1 | 1 | zero | 2 | O | N | $-CF_2-CF_2H$ |

The compounds having formula (I) can be obtained by different processes.

A process for the preparation of compounds of formula (I) consists in submitting to a transketalization reaction the ketals of formula:

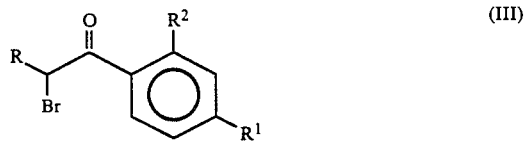

with an α-bromoketone having the formula:

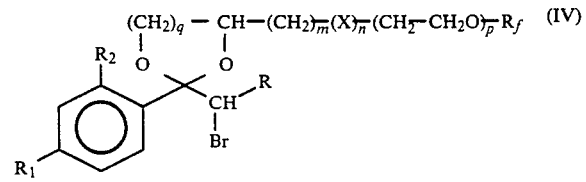

wherein R, R¹, R² have the meanings as specified above, with an acidic catalyst, such as sulphuric or p-toluenesulphonic acid, at temperatures comprised within the range of from 60° C. to 140° C. and in condensing the intermediate obtained, of formula:

with an alkali-metal salt of an azole having the formula:

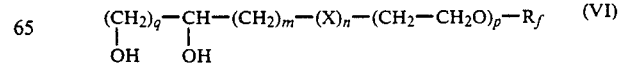

wherein M is an alkali-metal and A has the meaning indicated hereinabove, in a dipolar aprotic solvent, such as, e.g., dimethylformamide or dimethylsulphoxide, at temperature comprised within the range of from 20° C. to the reflux temperature of the reactants.

α-bromoketones of general formula (III) are compounds known [Lutz et al., J. Org. Chem. 12 (1947) 617; Ham, Reid, Jamieson, J.A.C.S. 52 (1930) 818; Brown, Mann, J.C.S. (1948) 847; Cowper, Davidson, Org. Synth. Coll vol. II (1943) 480].

Another process for the preparation of the compounds of formula (I) consists in submitting to hydrolysis with aqueous mineral acids, such as, e.g., HCl or H₂SO₄, at temperatures comprised within the range of from 20° C. to their boiling temperatures, the ketals of formula (II) and in reacting the so-obtained diol, having the formula:

$$(CH_2)_q-CH-(CH_2)_m-(X)_n-(CH_2-CH_2O)_p-R_f \quad (VI)$$
$$\phantom{(CH_2)_q-}|\phantom{CH-(CH_2)_m-(X)_n-(CH_2-CH_2O)_p-}|$$
$$\phantom{(CH_2)_q-}OH\phantom{-CH-(CH_2)_m-(X)_n-(CH_2-CH_2O)_p-}OH$$

with an α-azolylketone having the formula:

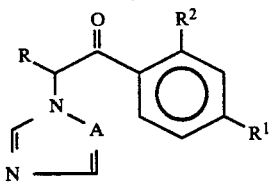

(VII)

The reaction of acetalization between compound (VI) and compound (VII) can be carried out by following techniques analogous to those described in technical literature, for example for the preparation of 2,4-diphenyl-1,3-dioxolane (Synthesis, 1974 (I) 23).

A convenient way for performing the reaction is refluxing the reactants for many hours, while azeotropically removing water, in a suitable solvent such as toluene or xylene, preferably in the presence of an alcohol, such as butanol, and in the presence of a strong acid, such as 4-methylbenzenesulphonic acid. As an alternative route, this reaction can be carried out, by starting from simple, linear or cyclic ketals, derived from α-azolylketones of type (VII), such as dimethyl or diethyl ketal or cyclopentylidene or cyclohexylidene ketal, by reaction with an excess of diol of type (VI), under the same experimental conditions as seen above.

The intermediate compounds having the general formula (II) can be prepared according to various methods:

(a) a process for the preparation of the compounds of formula (II) wherein either n is 1 or p is 1, consists in reacting a compound having the general formula:

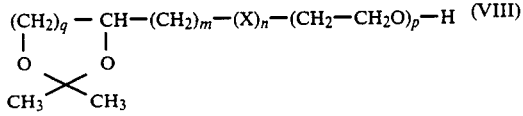

(VIII)

wherein m, n, p and q have the meaning indicated at claim 1, provided either n or p is 1, with fluoroolefin having the formula:

(IX)

wherein $X_1$ is Cl, F, $CF_3$ and $X_2$ is F, $CF_3$, to yield the compounds having the formula:

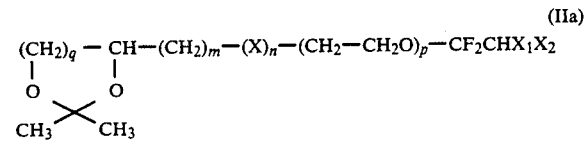

(IIa)

The compounds having the formula (VIII) can be prepared by known methods [(E. Fischer, Berichte 28, 1169; A.K.M. Anisuzzan, J. Chem. Soc. (c), 1021 (1967)]. As the fluoroolefins of formula (IX), perfluoroethylene, trifluorochloroethylene, perfluoroisobutene and perfluoropropene can be used. The reaction is generally carried out in a dipolar aprotic solvent, such as, e.g., dimethylformamide, or in an alcoholic solvent, such as tert.butanol, in the presence of catalytic or stoichiometric amounts of a strong base, such as sodium hydride, at temperatures comprised within the range of from 0° C. to 100° C.

(b) A further process for the preparation of the intermediate compounds having formula (II), wherein either n or p are equal to 1, consists in submitting to dehydrohalogenation the compounds having formula (IIa), to yield the unsaturated compounds of formula:

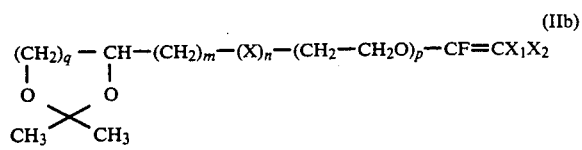

(IIb)

(c) A process for the preparation of compounds of formula (II) when the indices n and p are both equal to zero, consists in condensing an aldehyde having the formula:

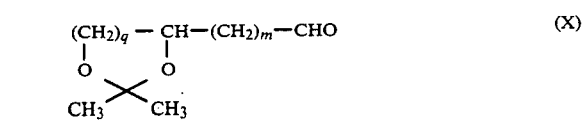

(X)

with a polyfluoroalkane of formula:

(XI)

wherein: $X_3$, $X_4$, equal to or different from each other, are F, Cl or Br, $X_5$ is a $C_1$-$C_3$-polyfluoroalkyl, Z is Br, I or also Cl when $X_3$ and $X_4$ are F, Cl, in an aprotic dipolar solvent, such as DMF, dioxane or THF, in the presence of a divalent metal, such as Zn or Mg, of a salt of a divalent metal or of such a Grignard's compound, as an alkyl- or arylmagnesium halide, and submitting to reduction, by known methods, the resulting carbinols, having the formula:

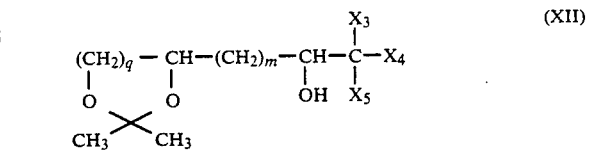

(XII)

to yield the unsaturated compounds of formula:

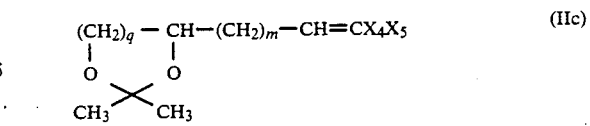

(IIc)

The aldehyde of formula (X) can be obtained by known methods [(e.g., E. Baer, Biochem. Piepu 3, 31 (1952)]. The reduction of carbinols (XII) to alkenes (IIc) is carried out by using methods known from technical literature, such as, e.g.:

1) Direct treatment of carbinol with zinc in acetic acid;
2) Conversion of the carbinol into acetate or into dihalophosphite and subsequent treatment with zinc in a dipolar aprotic solvent, such as DMF, in particular by the reduction of the acylated compound having the formula:

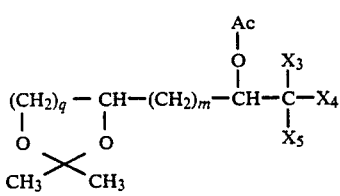

3) Replacement of the hydroxy group of carbinol with a halogen atom, and subsequent dehalogenation by zinc.

In the above mentioned conversions, in general, using the carbinol in the same reaction medium wherein it was prepared is possible.

(d) A further process for the preparation of the intermediates of formula (II) wherein indices n and p are equal to 0, consists in reducing a compound of formula (IIc), to yield the compounds of formula:

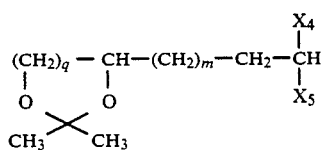

The reduction can be carried out by known methods, by using, e.g., LiAlH$_4$, NaBH$_4$, Zn/acids, Na amalgam, hydrogen and such catalysts as palladium and Ni-Raney.

(e) A further process for the preparation of intermediates (II) wherein n and p are 0, consists in dehydroalogenating, by a strong basis, in a polar aprotic solvent, at temperatures comprised within the range of from room temperature to the boiling temperature, the compound of formula (IIc), to yield the compound of formula:

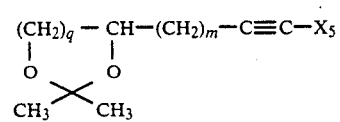

The reaction is carried out in solvents of ether type, such as DMF, THF, diethyl ether and with a strong basis, such as NANH$_2$, at room temperature, or at boiling temperature, according to the nature of the alkene (IIc).

Furthermore, the intermediates having formula (IV), when n or p is equal to 1, can be obtained also by the condensation of the compound having formula (VIII) with the α-bromoketone having formula (III), and subsequent reaction of the product obtained, of formula:

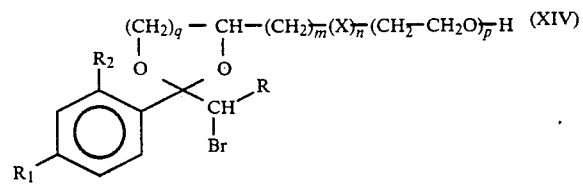

with a fluoroolefin having formula (IX) according to a reaction route similar to that indicated under method (a).

Alternatively, the compounds having the general formula (I), when n and/or p are equal to 1, can be obtained by addition of the compound having formula:

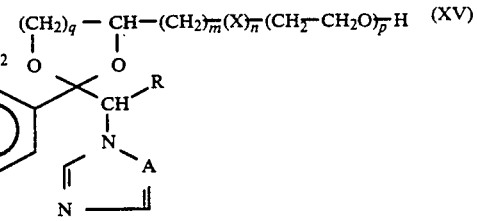

to a fluoroolefin of formula (IX) according to a reaction scheme analogous to that indicated under method (a).

Furthermore, the compounds having general formula (I), when R$_f$ is polyfluoroalkyl- (or alkenyl-) -methyl, can be advantageously prepared by the reaction of an alcohol of general formula:

$$R_f\text{—OH} \qquad (XVI)$$

wherein R$_f$ is a polyfluoroalkyl- (or -alkenyl-) -methyl, with a reactive ester having the general formula:

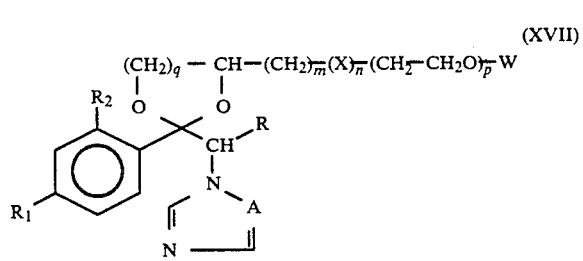

wherein m and/or p are equal to 1, and -OW represents a leaving group, such as, e.g., paratoluenesulphonate or methylsulphate.

The reaction is carried out by reacting an alkali-metal salt of alcohol (XVI) with ester XVII), in a dipolar aprotic solvent, such as, e.g., DME and HMPA, at temperatures comprised within the range of from 30° C. to 150° C.

The compounds having general formula (I) are endowed with fungicidal activity particularly high against phytopathogenous fungi which attack cultivations of cereals, of Cucurbitaceae, of grapevine and of fruit-trees.

Examples of plant diseases which can be fought by the compounds of the present invention are the following:

*Erysiphe graminis* on cereals;
*Sphaerotheca fuliginea* of Cucurbitaceae (e.g., of cucumber)
*Puccinia* on cereals
*Septoria* on cereals
*Helminthosporium* on cereals
*Rhyncosporium* on cereals
*Podosphaera leucotricha* on apple-tree
*Uncinula necator* on grapevine
*Venturia inaequalis* on apple-tree
*Piricularia oryzae* on rice

*Botrytis cinerea*
*Fusarium* on cereals and still further diseases.

The compounds having formula (I) are furthermore endowed with other positive characteristics, such as a fungicidal activity both curative and preventive in character, as well as a complete tolerability by the plants to be protected against the fungal infection.

Besides the high fungicidal activity with preventive and curative application, the compounds of formula (I) are characterized by systemic properties.

These properties allow the products to enter the vascular systems of plants, and act in sites (e.g., leaves) even very remote from those to which they are applied (e.g., roots).

For the practical uses in agriculture, having available fungicidal compositions containing one or more compounds of formula (I) as the active substance is often useful.

The application of these composition can be carried out on any part of the plants, e.g., on leaves, stems, limbs and roots, or on the same seeds, before the sowing, or also on the soil the plant is growing on. Compositions can be used, which have the form of dry powders, wettable powders, emulsifiable concentrates, pastes, granulates, solutions, suspensions, and so forth: the selection of the type of composition shall depend on the specific use. The compositions are prepared in known way, e.g., by diluting or dissolving the active substance with a solvent means and/or a solid diluent, optionally in the presence of surface-active agents. As solid diluents, or carriers, used can be: silica, kaolin, bentonite, talc, fossil flour, dolomite, calcium carbonate, magnesia, gypsum, clays, synthetic silicates, attapulgite, sepiolite. As liquid diluents, besides of course water, various types of solvents can be used such as, e.g., aromatic solvents (benzene, xylenes or mixtures of alkylbenzenes), chloroaromatic solvents (chlorobenzene), paraffins (petroleum fractions), alcohols (methanol, propanol, butanol), amines, amides (dimethylformamide), ketones (cyclohexanone, acetophenone, isophorone, ethyl-amyl-ketone), esters (isobutyl acetate). As surfactants: sodium, calcium or triethanolamine salts of alkylsulphates, alkylsulphonates, alkyl-arylsulphonates, polyethoxylated alkylphenols, fatty alcohols condensed with ethylene oxide, polyoxyethylated fatty acids, polyoxyethylated sorbitol esters, polyoxyethylated fats, lignine sulphonates can be used. The compositions can also contain special additives for particular purposes, e.g., such adhesive-properties-conferring agents as gum arabic, polyvinyl alcohol, polyvinylpyrrolidone.

If desired, to the compositions of the present invention also other compatible active substances as fungicides, phytomedicines, phytoregulators, herbicides, insecticides, fertilizers can be added.

The concentration of active substance in the said compositions can vary within a wide range, according to the active compound, to the cultivation, to the pathogen agent, to the environmental conditions and to the type of formulation adopted. In general, the concentration of active substance varies from 0.1 to 95%, preferably from 0.5 to 90% by weight.

The following examples illustrate the invention.

EXAMPLE 1

Preparation of
2-(2,4-dichlorophenyl)-2-(1,2,4-triazolyl)-methyl-4-(1,1,2,2-tetrafluoroethoxy)-methyl-1,3-dioxolane
(diastereoisomer A) (Compound No. 1)

Sodium hydride (1.7 g in oil suspension at 55–60%) is added to the triazole solution (2.4 g) in anhydrous DMF (25 ml), under nitrogen atmosphere, at 0° C.

The temperature is then allowed to rise to room temperature, and subsequently a solution is added of 8 g of 2-(2,4-dichlorophenyl)-2-bromomethyl-4-(1,1,2,2-tetrafluoroethoxy)-methyl-1,3-dioxolane in DMF (10 ml), prepared according to as described at Example 7.

The reaction mixture is heated at 130° C. for 6 hours. The reaction mixture is poured into water, and is extracted with ether. The organic extract is separated, washed again with water, dried over $Na_2SO_4$ and evaporated to dryness, to yield a dark-coloured oil (7.1 g), which is chromatographed over silica gel with first 9:1, then 1:1 n-hexane/ethyl acetate mixture, as the eluent. 1.1 g of a reddish oil is isolated, which is characterized as 2-(2,4-dichlorophenyl)-2-(1,2,4yl-4-(1,1,2,2-tetrafluoroethoxy)-methyl-1,3-dioxolane (diastereoisomer A) (Compound No. 1).

I.R. ($cm^{-1}$): 1500, 1280, 1210, 1110.
$^1$H-N M.R. (60 MHz) TMS in $CCl_4$. δ:
3.60–4.55 (m, 4 H); 4.00–4.45 (m, 1 H); 4.75 (s.broad, 2 H);
5.90 (tt, 1 H); 7.10–7.65 (m, 3 H); 7.80 (s, 1 H); 8.10 (s, 1 H).

EXAMPLE 2

Preparation of
2-(2,4-dichlorophenyl)-2-(1,2,4-triazolyl)-methyl-4-(1,1,2,2-tetrafluoroethoxy)-methyl-1,3-dioxolane
(mixture of diastereoisomers A+B) (Compound No.3)

The process described at Example 1 is repeated with the only variant that the deep-coloured oil obtained from the reaction is eluted over silica gel for a longer time, 4 g being obtained of reddish oil, characterized as a mixture of diastereoisomers A+B of the compound indicated at Example title.

Such characterization results from the following spectroscopic data:

I.R. coincident with that of compound No. 1 (Diastereoisomer A).
$^1$H-N.M.R. (60 MHz) TMS in $CCl_4$.δ:
3.60–4.55 (m, 4 H); 4.00–4.45 (m, 1 H); 4.75 (s.broad, 2 H);
5.65 and 5.90 (2tt, 1 H)., 7.10–7.65 (m, 3 H); 7.80 (s, 1 H);
8.10 (s, 1 H).

From the elution tails, diastereoisomer B, indicated in Table 1 as Compound No. 2, is isolated.

EXAMPLE 3

Preparation of
2-(4-chlorophenyl)-2-(1,2,4-triazolyl)-methyl)-4-(perfluoroprop-1-eneoxy)-methyl-1,3-dioxolane
(Compound No. 5) and of
2-(4-chlorophenyl)-2-(1,2,4-triazolyl)-methyl)-4-(1,2,3,3,3-hexafluoropropyloxy)-methyl-1,3-dioxolane
(Compound No. 6)

Potassium tert-butoxide is added in catalytic amount to a solution of 2-(4-chlorophenyl)-2-(1,2,4-triazolyl)- methyl-4-hydroxymethyl-1,3-dioxolane (4 g) in anhydrous tert-butanol (40 ml) and anhydrous tetrahydrofuran (80 ml), at 0° C., under nitrogen atmosphere.

The reaction equipment is evacuated, into it perfluoropropene is introduced at −10° C., and the reaction mixture is kept at this temperature for 2 hours, and then at room temperature for further 10 hours.

The reaction mixture is evaporated and the residue obtained is dissolved with methylene chloride and water.

The organic phase is separated, is dried over sodium sulphate, is evaporated to dryness, yielding a dark-coloured oil (5.5 g), which is chromatographed over silica gel, as the eluent a 1:1 n-hexane/ethyl acetate being used.

2,4 g is isolated of an orange-coloured oil, which is characterized as a mixture of compounds No. 5 and No. 6.

Compound No. 5, isolated, shows the following characteristics:

I.R. (cm$^{-1}$): 1760, 1500, 1200, 1050;

$^1$H-N.M.R.(60 MHz) TMS in CCl$_4$. δ: 3.50–3.90 (m, 4 H); 3.90–4.35

(m, 1 H); 4.45 (s. broad, 2 H); 7.40 (s, 4 H); 7.70 (s, 1 H); 8.10 (s, 1 H).

Compound No. 6, isolated, shows an I.R. spectrum similar to that of Compound No. 5, with the exception of the band at 1760 cm$^{-1}$, which is absent., and an N.M.R spectrum which displays, in addition to the signals indicated for compound No. 5, also a δ=4,7 (dm, 1 H).

EXAMPLE 4

Preparation of
2-(2-4-dichlorophenyl)-2-(1,2,4-triazolyl)-methyl-4-perfluoropropene-1-oxymethyl-1,3-dioxolane (Compound No. 7) and of
2-(2-4-dichlorophenyl)-2-(1,2,4-triazolyl)methyl-(1,1,2,3,3,3-hexafluoropropyl) oxymethyl-1,3-dioxolane (Compound No. 8)

The above said compounds have been obtained as a mixture by starting from 2-(2-4-dichlorophenyl)-2-(1,2,4-triazolyl)methyl-4-hydroxymethyl-1,3-dioxolane and perfluoropropene, and by a process analogous to that as described at Example 3.

Compound No. 7, isolated, has shown: I.R. (cm$^{-1}$): 1760, 1510, 1200, 1050;

$^1$H-N.M.R.(60 MHz) TMS in CCl$_4$. δ: 3.45–3.55 (m, 5 H); 4.70 (m, 2 H); 7.10–7.65 (m, 3 H); 7.70 (s, 1 H); 8.10 (s, 1 H).

Compound No. 8, isolated, has shown an I.R. spectrum similar to that of Compound No. 7, with the exception of the band at 1760 cm$^{-1}$, which results absent; and an N.M.R. spectrum which displays, in addition to the signals indicated for compound No. 7, also a δ=4,7 (dm, 1 H).

EXAMPLE 5

Preparation of
2-(4-chlorophenyl)-2-(1,2,4-triazolyl)methyl-4-(1,1,2,2-tetrafluoroethoxy)ethyl-1,3-dioxolane (Compound No. 9)

Sodium hydride (0.2 g in suspension in oil at 80%) is added to a solution of 2-(4-chlorophenyl)-2-(1,2,4-triazolyl)methyl-4-hydroxyethyl-1,3-dioxolane (4 g in anhydrous DMF (50 ml), at 0° C., under nitrogen.

The temperature is then allowed to rise back to room temperature and the reaction mixture is stirred for 1 hour.

After cooling again to 0° C., the reaction equipment is evacuated, perfluoroethylene is added, and the whole is left standing under an atmosphere of this gas for 5 hours.

The reaction mixture is then poured into water, and extracted with methylene chloride; the organic extract is separated and washed with water, dried over sodium sulphate and evaporated . to dryness. The residue obtained (5.2 g) is chromatographed over silica gel, as the eluent 1:1 n-hexane/ethyl acetate being used.

3.1 g is isolated of a yellow oil, which is characterized as 2-(4-chlorophenyl)-2-(1,2,4-triazolylmethyl)-4-tetrafluoroethoxyethyl-1,3-dioxolane.

I.R. (cm$^{-1}$): 1500, 1280, 1200, 1120;

$^1$H-N.M.R.(60 MHz) TMS in CCl$_4$. δ:

1.65 (m, 2 H); 3.30–4.20 (m, 5 H); 4.35 (s. broad, 2 H); 5.65

(tt, 1 H); 7.45 (s, 4 H); 7.65 (s, 1 H); 8.00 (s, 1 H).

EXAMPLE 6

Preparation of
2-(2,4-dichlorophenyl)-2-(1,2,4-triazolyl)-methyl-4-(1,1,2-trifluoro-2-chloroethoxy)methyl-1,3-dioxolane (Compound No. 17) and of
2-(2,4-dichlorophenyl)-2-(1,2,4)-triazolyl)methyl-4-(1,2-difluoro-2-chloroetheneoxy)-methyl-1,3-dioxolane (Compound No. 18)

The above indicated compounds have been prepared by following a process analogous to that as described at Example 5, by starting from 2-(2-4-dichlorophenyl)-2-(1,2,4-triazolyl)methyl-4-hydroxymethyl-1,3-dioxolane and monochlorotrifluoroethylene.

Compound No. 17 is characterized by:

I.R. (cm$^{-1}$): 1600, 1270, 1170, 1130, 1050;

$^1$H-N.M.R.(60 MHz) TMS in CDCl$_3$. δ:

3.55–4.30 (m, 5 H); 4.70 (s.broad, 2 H); 5.85 (dt, 1 H); 7.00–7.65

(m, 3 H); 7.75 (s, 1 H); 8.05 (s, 1 H).

Compound No. 18 is characterized by:

I.R. (cm$^{-1}$): 1760, 1510, 1280, 1180, 1040;

$^1$H-N M.R.(60 MHz) TMS in CDCl$_3$. δ:

3.55–4.50 (m, 5 H); 4.75 (s.broad, 2 H); 7.00–7.60 (m, 3 H);

7.75 (s, 1 H); 8.10 (s, 1 H).

EXAMPLE 7

By following processes analogous to those as described in the preceding Examples, the compounds indicated in Table 1 with the numbers: 4, 10-16, 19, 20 and 21 have been prepared. The N.M.R. spectra of such compounds are reported hereunder:

Compound No. 4

$^1$H-N.M.R.(60 MHz) TMS in CCl$_4$.δ:

3.50–4.00 (m, 4 H); 4.00–4.35 (m, 1 H); 4.50 (s.broad, 2 H);

5.90 (tt, 1 H); 7.45 (s, 4 H); 7.75 (s, 1 H); 8.15 (s, 1 H).

Compound No. 10

$^1$H-N.M.R.(60 MHz) TMS in CDCl$_3$. δ:

1.45–1.90 (m, 2 H); 3.65–4.30 (m, 5 H); 4.70 (s.broad, 2 H);

5.60 (tt, 1 H); 7.00–7.60 (m, 3 H); 7.80 (s, 1 H); 8.05 (s, 1 H).

Compound No. 11

¹H-N.M.R.(200 MHz) TMS in CDCl₃. δ:
3.6–3.9 (m, 4 H); 3.9–4.3 (m, 1 H); 4.58 and 4.62 (2 s, 2 H);
5.2–6 (2tt, 1 H); 6.7–7.5 (m, 3 H); 7.82 and 7.85 (2 s, 1 H);
8.1 (s, 1 H).

Compound No. 12

¹H-N.M.R.(60 MHz) TMS in CDCl₃.δ:
3.5–4.4 (m, 5 H); 4.45 (s.broad, 2 H); 5.8 (tt, 1 H); 7–7.65
(m, 3 aromatic H's + 3 imidazolic H's).

Compound No. 13

¹H-N.M.R.(60 MHz) TMS in CDCl₃. δ:
3.6–4.2 (m, 5 H); 4.45 (s.broad, 2 H); 5.6 (tt, 1 H); 6.9–7.8
(m, 3 aromatic H's + 3 imidazolic H's).

Compound No. 15 ¹H-N.M.R.(60 MHz) TMS in CDCl₃. δ:

1.20–2.00 (m, 2 H); 3.20–4.20 (m, 5 H); 4.35 (s.broad, 2 H);
4.90 (dm, 1 H); 7.30 (s, 4 H); 7.75 (s, 1 H); 8.00 (s, 1 H).

Compound No. 16

¹H-N.M.R.(60 MHz) TMS in CDCl₃. δ:
1.30–2.00 (m, 2 H); 3.20–4.50 (m, 5 H); 4.65 (s.broad, 2 H);
5.10 (dm, 1 H); 7.00–7.70 (m, 3 H); 7.80 (s, 1 H); 8.05 (s, 1 H).

Compound No. 19:

¹H-N.M.R.(60 MHz) TMS in CDCl₃. δ:
3.15–3.45 (m, 2 H); 3.50–4.30 (m, 7 H); 4.75 (s.broad, 2 H);
5.75 (tt, 1 H); 7.00–7.65 (m, 3 H); 7.80 (s, 1 H); 8.15 (s, 1 H).

Compound No. 20

¹H-N.M.R.(60 MHz) TMS in CDCl₃. δ:
3.20–4.30 (m, 9 H); 4.70 (s.broad, 2 H); 5.55 and 5.70 (2 tt, 1 H); 7.05–7.75 (m, 3 H); 7.80 (s, 1 H); 8.15 (s, 1 H).

Compound No. 21

¹H-N.M.R.(60 MHz) TMS in CDCl₃. δ:
0.80–1.90 (m, 2 H); 3.40–4.20 (m, 5 H); 4.45 (s, 2 H); 5.70
(tt, 1 H); 7.00–7.50 (m, 3 H); 7.70 (s, 1 H); 8.15 (s, 1 H).

EXAMPLE 8

Preparation of
2-(2,4-dichlorophenyl)-2-bromomethyl-4-(1,1,2,2-tetrafluoroethoxy)methyl-1,3-dioxolane.

Sodium hydride (0.48 g in suspension in oil at 55–60%) is added to 2-(2,4-dichlorophenyl)-2-bromomethyl-4-hydroxymethyl-1,3-dioxolane (8.9 g) dissolved in anhydrous DMF (90 ml), at 0° C., under nitrogen.

The temperature is then allowed to rise back to room temperature and the reaction mixture is stirred for 30 minutes.

After cooling again to 0° C., the reaction equipment is evacuated, perfluoroethylene is added, and the whole is left standing under an atmosphere of this gas for 20 hours, at room temperature.

The reaction mixture is then poured into water, and extracted with ethyl ether; the ether extract is washed with water, dried over sodium sulphate and evaporated to dryness.

A reddish oil is obtained (8.5 g), which is used as such for the reaction according to Example 1.

I.R. (cm⁻¹): 1280, 1210; 1120;
¹H-N.M.R.(60 MHz) TMS in CDCl₄. δ:
3.80 (s.broad, 2 H); 3.90–4.70 (m, 5 H); 5.50 and 5.70 (2 tt, 1 H); 7.10–7.70 (m, 3 H).

EXAMPLE 9

Preparation of
2-(2,4-dichlorophenyl)-2-bromomethyl-4-(1,1,2,2-tetrafluoroethoxy)methyl-1,3-dioxolane A mixture of 4-(1,1,2,2-tetrafluoroethoxy)methyl-2,2-dimethyl-1,3-dioxolane (6.8 g), 2-bromo-1-(2,4-dichlorophenyl)ethanone (6 g.), sulphuric acid (0.3 ml at 96%) is heated at 120° C. for 3 hours, the acetone being formed in the reaction being distilled off.

After cooling, the reaction mixture is diluted with methylene chloride and washed with water; the organic phase is then dried over sodium sulphate; and evaporated to dryness.

A dark-coloured oil is obtained (8.8 g), which has I.R. and N.M.R. spectra identical to those of compound prepared at Example 8.

EXAMPLE 10

Preparation of
4-(1,1,2,2-tetrafluoroethoxy)methyl-2,2-dimethyl-1,3-dioxolane.

Sodium hydride (0.91 g in suspension in oil at 50%) is added to the solution of 4-hydroxymethyl-1,3-dioxolane (5 g) in anhydrous DMF (70 ml), at 0° C., under nitrogen.

The temperature is then allowed to rise back to room temperature and the reaction mixture is stirred for 30 minutes.

After evacuating the reaction equipment, perfluoroethylene is added; the whole is left standing under an atmosphere of this gas for 20 hours, the exothermic heat initially evolved being absorbed, so to avoid a temperature increase.

The reaction mixture is then poured into water, and extracted with ethyl ether; the ether extract is washed with water, dried over sodium sulphate and evaporated to dryness.

An orange-coloured oil is obtained (5 g), which is used as such for the reaction according to Example 9.

I.R. (cm⁻¹): 1270, 1210, 1120, 1090.
¹H-N.M.R.(60 MHz) TMS in CCl₄. δ:
1.35 (s, 3 H); 1.40 (s, 3 H); 3.65–4.50 (m, 5 H); 5.75 (tt, 1 H).

EXAMPLE 11

Preparation of
2-(4-chlorophenyl)-2-(1,2,4-triazolyl)methyl-4-hydroxymethyl-1,3-dioxolane.

To a mixture constituted by 11 g of 1,2,3-propanetriol, 5 g of paratoluenesulphonic acid, 100 ml of n-butanol and 500 ml of toluene, 10 g is added of 2-(1,2,4-triazolyl)-1-(4-chlorophenyl)ethanone. The whole is refluxed for 60 hours, water being azeotropically distilled off.

After cooling, the reaction mixture is treated with a solution of sodium hydroxide solution at 20%, it is then poured into water, and ethyl ether is added.

The organic phase is separated, washed with water, dried over sodium sulphate and evaporated to dryness. The residue obtained is treated with isopropyl ether, to yield a light-coloured solid (8 g), having a melting point of 115°–117° C. and characterized by the following spectra:

I.R. (cm$^{-1}$): 3200, 1510, 1050.
$^1$H-N.M.R. (60 MHz), TMS in CDCl$_3$, δ:
3.30–4.20 (m, 6 H, one of which swaps with D$_2$O); 4.5 (s.broad, 2 H); 7.45 (s, 4 H); 7.90 (s, 1 H); 8.25 (s, 1 H).

EXAMPLE 12

Preparation of 2-(2,4-dichlorophenyl)-2-(1,2,4-triazolyl)-methyl-4-hydroxymethyl-1,3-dioxolane.

Potassium iodide (0.75 g) and 2-(2,4-dichlorophenyl)-2-bromomethyl-4-hydroxymethyl-1,3-dioxolane (5 g) dissolved in anhydrous DMF are added to a solution of potassium triazolate (4 g) in anhydrous DMF (20 cc), at room temperature, under nitrogen.

The whole is heated at 130° C. for 6 hours.

The reaction mixture is poured into water and is extracted with ethyl acetate. The organic phase is separated, washed with water, dried over sodium sulphate, evaporated to dryness, to yield a dark-coloured solid (5.1 g), which is chromatographed over silica gel, the elution being performed first with 1:1 n-hexane/ethyl acetate, and then with pure ethyl acetate.

A light-coloured oil (1.1 g) is isolated, which turns into a solid by treatment with isopropyl ether.

M.p.: 98°–100° C.
I.R. (cm$^{-1}$): 3300, 1510, 1050.
$^1$H-N.M R. (60 MHz), TMS in CDCl$_3$. δ:
3.20–4.50 (m, 6 H, one of which swaps with D$_2$O); 4.80
(s.broad, 2 H); 7.15–7.70 (m, 3 H); 7.90 (s, 1 H); 8.25 (s, 1 H).

EXAMPLE 13

Preparation of 2-(4-chlorophenyl)-2-(1,2,4-triazolyl)methyl-4-hydroxyethyl -1,3-dioxolane.

Sodium hydride (7.4 g in suspension in oil at 80%) is added proportionately to a solution of triazole (16.7 g) in anhydrous DMF (100 ml), at 0° C., under nitrogen.

The temperature is then allowed to rise back to room temperature; subsequently a solution is added dropwise of 2-(4-chlorophenyl)-2-bromomethyl-4-hydroxyethyl-1,3-dioxolane (26.5 g) in anhydrous DMF (60 ml).

The whole is heated at 120° C. for 11 hours.

The reaction mixture is poured into water and is extracted with ethyl acetate. The organic phase is separated and washed more times with water; the product is then extracted with 1:4-diluted hydrochloric acid. The aqueous solution is made alkaline with sodium hydroxide at 20% and is extracted with ethyl acetate. The organic extract is separated, dried over sodium sulphate, evaporated to dryness; the residue obtained is treated with isopropyl ether to yield a light-coloured solid (7.4 g), having a m.p. of 104°–106° C., and the following spectra:

I.R. (cm$^{-1}$): 3250, 1515, 1060.
$^1$H-N.M.R. (60 MHz), TMS in CDCl$_3$. δ:
1.65 (m, 2 H); 2.90 (s, 1 H which swaps with D$_2$O); 3.20–4.30
(m, 5 H); 4.50 (s.broad, 2 H); 7.40 (s, 4 H); 7.90 (s, 1 H);
8.25 (s, 1 H).

EXAMPLE 14

Preparation of 2-(4-chlorophenyl)-2-bromomethyl-4-hydroxyethyl-1,3-dioxolane.

A mixture of 1,2,4-butanetriol (18 g), paratoluenesulphonic acid (2.5 g), n-butanol (50 ml), toluene (250 ml), 2-bromo-1-(4-chlorophenyl)-ethanone (33 g) is refluxed for 25 hours, water being distilled off azeotropically.

After cooling, the reaction mixture is treated with a solution of potassium carbonate; the organic phase separated is then washed with water, dried over sodium sulphate, and evaporated to dryness.

A reddish oil is obtained (42.2 g) which is used as such for the reaction according to Example 13.

I.R. (cm$^{-1}$): 3400, 1100, 1050, 1020.
$^1$H-N M.R. (60 MHz), TMS in CCl$_4$, δ:
1.70 (m, 2 H); 2.80 (s, 1 H which swaps with D$_2$O); 3.55 (s, 2 H); 3.55–4.50 (m, 5 H); 7.40 (m, 4 H);

EXAMPLE 15

Determination of the fungicidal activity against cucumber oidium (*Sphaerotheca fuliginea* (Sclech) Salmon)

Preventive activity:

Cucumber plants, cv. Marketer, grown in pot in conditioned environment, have been sprinkled on the lower faces of their leaves with the product under test in water-acetonic solution at 20% (v/v) of acetone. The plants have been subsequently kept in conditioned environment for 1 day, and have been then sprinkled on the upper face of the leaves with an aqueous suspension of conidia of *Sphaerotheca fuliginea* (200,000 conidia per ml). The plants have been then placed again in conditioned environment.

At the end of the incubation time of the fungus (8 days), the severity of the infection has been evaluated, and it has been given a rating based on an evaluation scale going from 100 (=healthy plant) to 0 (=completely infect plant).

Curative activity:

Plants of cucumber cv. Marketer, grown in pot in conditioned environment, have been sprayed on the upper face of the leaves with an aqueous solution of conidia of *Sphaerotheca fuliginea* (200,000 conidia per ml) After 24 hours from the infection, the plants have been treated with the products under test in water-acetonic solution at 20% (v/v of acetone), by spraying of both the faces of their leaves At the end of the incubation time of the fungus (8 days), during which the plants have been preserved in suitably conditioned environment, the severity of the infection has been evaluated, and it has been given a rating based on an evaluation scale going from 100 (=healthy plant) to 0 (=completely infected plant).

The results are reported in Table 2.

EXAMPLE 16

Determination of the fungicidal activity against the oidium of wheat (*Erysiphe graminis* D.C.)

Preventive activity:
The leaves of wheat, cv. Irnerio, grown in pot in conditioned environment, have been treated by sprinkling of both their faces with the products under test in water-acetonic solution at 20% (v/v) of acetone.

After one day of permanence in conditioned environment at 20° C, and 70% R.H., the plants have been sprinkled on both the faces of their leaves with an aqueous suspension of *Erysiphe graminis* (200,000 conidia per ml). After 24 hours of performance in a humidity-saturated environment, at 21° C., the plants have been kept in a conditioned environment for the incubation of the fungus.

At the end of said incubation period (12 days), the severity of the infection has been evaluated visually, and it has been given a rating based on an evaluation scale going from 100 (=healthy plant) to 0 (=completely infected plant).

Curative activity:
The leaves of wheat cv. Irnerio, grown in pot in conditioned environment, have been sprayed on both their faces with an aqueous suspension of *Erysiphe graminis* (200,000 conidia per ml). After 24 hours of permanence in humidity-saturated environment, at 21° C., the leaves have been treated with the products under test in water-acetonic solution at 20% (v/v of acetone), by spraying of both their faces.

At the end of the incubation time (12 days), the severity of the infection has been visually evaluated, and it has been given a rating based on an evaluation scale going from 100 (=healthy plant) to 0 (=completely infected plant).

The results are reported in Table 2.

EXAMPLE 17

Determination of the fungicidal activity against the linear rust of wheat (Puccinia graminis Pers.)

Preventive activity:
The leaves of wheat, cv. Irnerio, grown in pot in conditioned environment, have been treated by sprinkling of both their faces with the products under test in water-acetonic solution at 20% (v/v) of acetone. After one day of permanence in environment conditioned at 23° C. and 70% R.H., the plants have been sprinkled on both the faces of their leaves with a mixture of spores of *Puccinia graminis* in talc (100 mg of spores per 5 g of talc). After 48 hours of permanence in a humidity-saturated environment, at 21° C., the plants have been kept in a conditioned environment for the incubation of the fungus.

At the end of said incubation period (14 days), the severity of the infection has been evaluated visually, and it has been given a rating based on an evaluation scale going from 100 (=healthy plant) to 0 (=completely infected plant).

Curative activity:
The leaves of wheat cv. Irnerio, grown in pot in conditioned environment, have been sprayed on both their faces with a mixture of spores of of *Puccinia graminis* in talc (100 mg of spores/5 g of talc); after 48 hours of permanence in humidity-saturated environment, at 21° C., the leaves have been treated with the products under test in water-acetonic solution at 20% (v/v of acetone), by spraying of both their faces.

At the end of incubation time (14 days), the severity of the infection has been visually evaluated, and it has been given a rating based on an evaluation scale going from 100 (=healthy plant) to 0 (=completely infected plant).

The results are reported in Tables 2 and 3.

TABLE 2

| Compound No. | Dosis g/l | *Sphaerotheca fuliginea*/cucumber Preventive Activity | *Sphaerotheca fuliginea*/cucumber Curative Activity | *Erysiphe graminis* trit./wheat Preventive Activity | *Erysiphe graminis* trit./wheat Curative Activity | *Puccinia graminis*/wheat Preventive Activity | *Puccinia graminis*/wheat Curative Activity |
|---|---|---|---|---|---|---|---|
| 1 | 0.5 | 100 | 100 | 100 | 100 | 100 | 100 |
|   | 0.25 | 100 | 100 | 100 | 100 | 100 | 100 |
|   | 0.125 | 100 | 100 | 100 | 100 | 100 | 100 |
|   | 0.06 | 100 | 100 | 100 | 100 | 100 | 100 |
| 3 | 0.5 | 100 | 100 | 100 | 100 | 100 | 100 |
|   | 0.25 | 100 | 100 | 100 | 100 | 100 | 100 |
|   | 0.125 | 100 | 100 | 100 | 100 | 100 | 100 |
|   | 0.06 | 100 | 100 | 100 | 100 | 100 | 100 |
| 4 | 0.5 | 100 | 100 | 100 | 100 | 100 | 100 |
|   | 0.25 | 100 | 100 | 100 | 100 | 60 | 100 |
|   | 0.125 | 100 | 100 | 100 | 100 | 40 | 60 |
|   | 0.06 | 100 | 100 | 100 | 100 | 20 | 40 |
| 5 + 6 (mixture) | 0.5 | 100 | 100 | 100 | 100 | 100 | 100 |
|   | 0.25 | 100 | 100 | 100 | 100 | n.d. | 100 |
|   | 0.125 | 100 | 100 | 85 | 100 | 80 | 100 |
|   | 0.06 | 100 | 100 | n.d. | 100 | n.d. | 100 |
| 7 + 8 (mixture) | 0.5 | 100 | 100 | 100 | 100 | 100 | 100 |
|   | 0.25 | 100 | 100 | 100 | 100 | 100 | 100 |
|   | 0.125 | 100 | 100 | 100 | 100 | 100 | 100 |
|   | 0.06 | 100 | 100 | 100 | 100 | 90 | 100 |
| 9 | 0.5 | 100 | 100 | 100 | 100 | 100 | 100 |
|   | 0.25 | 100 | 100 | n.d. | 100 | n.d. | 100 |
|   | 0.125 | 100 | 100 | 70 | 100 | 40 | 100 |
|   | 0.06 | 100 | 100 |  | 100 |  | 85 |

TABLE 3

| Curative Activity against *Puccinia graminis*/Wheat | | | |
|---|---|---|---|
| Dosis, g/l | Compound No. 3 | Ref. Compound A | Ref. Compound B |
| 0.0018 | 100 | 80 | 0 |
| 0.00045 | 100 | 50 | 0 |

Ref. Compound A = 1-[2-(2,4-dichlorophenyl)-4-propyl-1,3-di-oxolan-2-yl-methyl]-1H-1,2,4-triazole (common name Propiconazole).
Ref. Compound B = 1-[(2-(2,4-dichlorophenyl)-4-(2-chloroeth-oxy)-1,3-dioxolan-2-yl-methyl]-1H-1,2,4-triazole (U.S. Pat. No. 4,338,327, compound No. 17, Table 1).

EXAMPLE 18

The preventive activities have been determined of compound No. 3 and of Propiconazole, against Puccinia graminis on wheat, with the same modalities as reported at Example 16, but with the variant that the treatment of leaves by the products has been carried out during the vegetative step of the earing and that the inoculation with the fungi has been carried out 21 days after said treatment. The results are shown in Table 4.

TABLE 4

| Preventive Activity against *Puccinia graminis*/Wheat | | | |
|---|---|---|---|
| Dosis, g/l | Compound No. 3 | Ref. Compound A | Ref. Compound B |
| 0.15 | 100 | 70 | 0 |
| 0.10 | 100 | 43 | 0 |

We claim:

1. Compound having the formula:

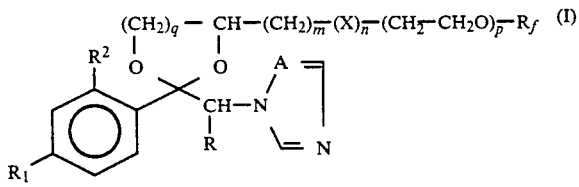

in their stereochemical isomer form, wherein:

$m = 0, 1, 2$; $n = 0, 1$ with the condition that when $m = 0$, also $n = 0$;

$p = 0$; $q = 1, 2$;

X is either oxygen or sulphur;

$A = N$;

R is H, $CH_3$, F;

$R_1$ is selected from the group consisting of chlorine, bromine, fluorine, $CF_3$, phenyl, $C_1$–$C_2$-alkoxy and $C_1$–$C_2$-haloalkoxy, wherein the halogen is Cl, Br, F;

$R_2$ is selected from the group consisting of H, chlorine, bromine and fluorine;

$R_f$ is selected from the group consisting of the group formed by alkyls containing from 1 to 4 carbon atoms, and containing at least 4 atoms of halogen selected from F, Cl and Br, of which at least 3 are F atoms; and alkenyls and alkynyls containing up to 4 carbon atoms, and containing halogen atoms selected from F Cl and Br of which at least 2 are F atoms.

2. Compound according to claim 1, which is 1-[2-(2,4-dichlorophenyl-4-(1,1,2,2-tetrafluoroethoxy)methyl-1,3-dioxolan-2-yl-methyl]-1 H-1,2,4-triazole.

3. Antifungal composition containing an effective amount of one or more compounds according to claim 1, together with an inert solid or liquid carrier.

4. Antifungal composition containing an effective amount of the compound 1-[2-(2,4-dichlorophenyl)-4-(1,1,2, 2-tetrafluoroethyloxy-methyl-1,3-dioxolan-2-ylmethyl]-1 H-1,2,4-triazole, together with an inert solid or liquid carrier.

5. Method for controlling fungal infestations in useful plants consisting in distributing on the plant, on the surrounding ground, when the fungal infestation is expected or is already in progress, an efficacious amount of a compound according to claim 1, as such or in the form of a suitable composition.

6. Method for controlling fungal infestations in useful plants consisting in distributing on the plant, on the surrounding ground, when the fungal infestation is expected or is already in progress, an efficacious amount of the compound 1-[2-(2,4-dichlorophenyl)-4-(1,1,2,2-tetrafluoroethyloxy)methyl-1,3-dioxolan-2-ylmethyl]-1 H-1,2,4-triazole according to claim 2, either as such, or in the form of a suitable composition.

* * * * *